US008845191B2

(12) United States Patent
Ngar et al.

(10) Patent No.: US 8,845,191 B2
(45) Date of Patent: Sep. 30, 2014

(54) COMPOUND 6D-OFFSET SIMULATING PHANTOM AND QUALITY ASSURANCE PROGRAM FOR PRECISION IMAGE-GUIDED RADIOTHERAPY AND RADIOSURGERY

(75) Inventors: Yuen Kan Ngar, Shatin (HK); Wai Sang Poon, Shatin (HK)

(73) Assignee: The Chinese University of Hong Kong, Shatin, New Territories, Hong Kong (CN)

( * ) Notice: Subject to any disclaimer, the term of this patent is extended or adjusted under 35 U.S.C. 154(b) by 275 days.

(21) Appl. No.: 13/599,907

(22) Filed: Aug. 30, 2012

(65) Prior Publication Data
US 2014/0016759 A1      Jan. 16, 2014

Related U.S. Application Data

(60) Provisional application No. 61/671,582, filed on Jul. 13, 2012.

(51) Int. Cl.
  *A61N 5/10*     (2006.01)
  *A61B 6/00*     (2006.01)
  *A61B 19/00*    (2006.01)

(52) U.S. Cl.
  CPC .............. *A61B 6/583* (2013.01); *A61B 19/50* (2013.01)
  USPC .............................. 378/207; 378/18; 378/205

(58) Field of Classification Search
  CPC ............ A61B 6/583; A61B 9/50; A61B 9/52; A61B 9/5244; A61B 5/1127; A61B 5/1048; A61B 5/1049

USPC ................... 378/207, 18, 205, 4, 17, 204, 20; 250/252.1, 396 R, 493.1; 600/427
See application file for complete search history.

(56) References Cited

U.S. PATENT DOCUMENTS

| | | | | | |
|---|---|---|---|---|---|
| 5,963,612 | A | * | 10/1999 | Navab | 378/4 |
| 6,049,582 | A | * | 4/2000  | Navab | 378/4 |
| 6,129,670 | A | * | 10/2000 | Burdette et al. | 600/427 |
| 6,256,529 | B1 | * | 7/2001 | Holupka et al. | 600/427 |
| 6,364,529 | B1 | * | 4/2002 | Dawson | 378/207 |

(Continued)

OTHER PUBLICATIONS

Cossman, Peter H., Advances in Image-guided Radiotherapy—The Future is in Motion. European Oncology Review, 2005, p. 30-34.

(Continued)

*Primary Examiner* — David A Vanore
(74) *Attorney, Agent, or Firm* — Kilpatrick Townsend & Stockton LLP

(57) ABSTRACT

This invention provides a device for checking the performance of an image-guided radiation therapy (IGRT) apparatus. The device (referred to here as a phantom) has a central body with detectable markers, rotatably suspended on a ball joint so that the pitch, roll, and yaw may be adjusted. The body is secured against a base plate, which in turn may be positioned laterally, longitudinally, and vertically within the patient treatment area. Thus, the phantom can be adjusted through six degrees of freedom so as to simulate patient positioning. To perform quality control, the phantom is secured at a predetermined offset, and the position is detected by the IGRT apparatus. The robotic couch is then allowed to compensate, a second measurement is made. The measured values are compared with the predetermined offset to assess both the accuracy in detecting the position of the phantom, and the accuracy of the mechanical correction.

25 Claims, 12 Drawing Sheets

(56) References Cited

U.S. PATENT DOCUMENTS

| | | | |
|---|---|---|---|
| 6,493,574 B1* | 12/2002 | Ehnholm et al. | 600/429 |
| 7,056,019 B1* | 6/2006 | Hanson et al. | 378/207 |
| 7,171,255 B2* | 1/2007 | Holupka et al. | 600/427 |
| 7,201,715 B2* | 4/2007 | Burdette et al. | 600/3 |
| 7,349,523 B2* | 3/2008 | Jenkins et al. | 378/65 |
| 7,510,325 B2* | 3/2009 | Endo et al. | 378/207 |
| 7,594,753 B2* | 9/2009 | Main et al. | 378/207 |
| 7,604,405 B2* | 10/2009 | Main et al. | 378/205 |
| 7,738,624 B2* | 6/2010 | Herold et al. | 378/18 |
| 7,778,392 B1* | 8/2010 | Berman et al. | 378/210 |
| 8,129,699 B2* | 3/2012 | Balakin | 250/492.3 |
| 8,244,064 B2* | 8/2012 | Boese et al. | 382/284 |
| 8,249,317 B2* | 8/2012 | Falco et al. | 382/128 |
| 8,598,543 B2* | 12/2013 | Balakin | 250/492.1 |
| 8,708,562 B1* | 4/2014 | Nosil | 378/207 |
| 8,791,435 B2* | 7/2014 | Balakin | 250/492.3 |
| 2006/0002519 A1* | 1/2006 | Jenkins et al. | 378/207 |
| 2007/0071176 A1* | 3/2007 | Main et al. | 378/207 |
| 2008/0144776 A1* | 6/2008 | Main et al. | 378/163 |
| 2013/0292580 A1* | 11/2013 | Schubert et al. | 250/395 |
| 2014/0016759 A1* | 1/2014 | Ngar et al. | 378/207 |
| 2014/0050375 A1* | 2/2014 | Baker et al. | 382/128 |

OTHER PUBLICATIONS

Jaffray et al., Flat-Panel Cone-Beam Computed Tomography for Image-Guided Radiation Therapy, Int J. Radiation Oncology Biol. Phys, 2002, vol. 53, No. 5, p. 1337-1349.

Dawson, LA et al., Image-guided radiotherapy: rationale, benefits, and limitations. Lancet Oncology, 2006, vol. 7, issue 10, p. 848-858.

Van Dyk, J., Modern Technology of Radiation Oncology. Madison, WI: Medical Physics Pub, 1999, Ch. 1, 30 pages.

Takakura T, Mizowaki T, et al. (2010) "The geometric accuracy of frameless stereotactic radiosurgery using a 6D robotic couch system" Phys. Med. Biol. 55 1-10.

Murphy M J (1997) "An automatic six-degree-of-freedom image registration algorithm for image-guided frameless stereotaxic radiosurgery" Med. Phys. 24 857-866.

Chang Z, Wang Z, et al. (2010) "6D image guidance for spinal non-invasive stereotactic body radiation therapy: Comparison between Exactrac X-ray 6D with kilo-voltage cone-beam CT" Radiother. Oncol. 95 116-121.

Yan H, Yin F F, et al. (2003) "A phantom study on the positioning accuracy of the Novalis body system" Med. Phys. 30 3052-3060.

Wurm R E, Erbel S, et al. (2008) "Novalis frameless image-guided noninvasive radiosurgery: initial experience" Neurosurgery 62 A11-17.

Verellen D, Soete G, et al. (2003) "Quality assurance of a system for improved target localization and patient setup that combines real-time infrared tracking and stereoscopic X-ray imaging" Radiother. Oncol. 67 129-141.

Teh B S, Paulino A C, et al. (2007) "Versatility of the Novalis System to Deliver Image-Guided Stereotactic Body Radiation Therapy (SBRT) for Various Anatomical Sites" Technology in Cancer Research and Treatment 6 347-354.

Ryu S, Yin F F, et al. (2003) "Image-guided and intensity-modulated radiosurgery for patients with spinal metastasis" Cancer 97 2013-2018.

Sahgal, Arjun M.D., et al. (2008) "Stereotactic Body Radiosurgery for Spinal Metastases: A Critical Review" Int. J. Radiation Oncology Biol. Phys. vol. 71, No. 3, pp. 652-665.

Yamada, Yoshiya et al. (2008) "High-Dose, Single-Fraction Image-Guided Intensity-Modulated Radiotherapy for Metastatic Spinal Lesions" Int. J. Radiation Oncology Biol. Phys. vol. 71, No. 2, pp. 484-490.

Avanzo M., Romanelli P. (2009) "Spinal Radiosurgery: Technology and Clinical Outcomes" Neurosurg Rev 32: pp. 1-13.

Agazaryan, Nzhde et al., (2008) "Image-guided radiosurgery for spinal tumors: methods, accuracy and patient intrafraction motion" Phys. Med. Biol. 53, pp. 1715-1727.

* cited by examiner

Figure 7

| Random Target Offsets for Quality Assurance | | | | | | | | | | | |
|---|---|---|---|---|---|---|---|---|---|---|---|
| Translations (mm) | | | Rotations (°) | | | Translations (mm) | | | Rotations (°) | | |
| VERT | LONG | LAT | YAW | ROLL | PITCH | VERT | LONG | LAT | YAW | ROLL | PITCH |
| 0 | 19 | -6 | 0.5 | 4 | 0.5 | -3 | 20 | 8 | 1 | 0 | -1 |
| -3 | 1 | -7 | -0.5 | 4 | 0 | -19 | 20 | 0 | 1 | 1 | 2 |
| -16 | -11 | -14 | 2.5 | -1.5 | 1.5 | -4 | 1 | -11 | -1 | -1.5 | 0 |
| 6 | 15 | 10 | 1 | -0.5 | -2 | 18 | 6 | -5 | 0 | 3.5 | 2 |
| -20 | 6 | 2 | 0.5 | 1 | -0.5 | 19 | -20 | 8 | -1.5 | 3 | -0.5 |
| 7 | -9 | 1 | -2.5 | 2.5 | 0.5 | -12 | -1 | -8 | -1 | -3 | 2 |
| -7 | -18 | 2 | 1.5 | -1 | 1.5 | 18 | 7 | -5 | 0.5 | 0.5 | 2 |
| -1 | -11 | -12 | 2.5 | 2.5 | -1.5 | 8 | 7 | -13 | 0 | -2.5 | 2.5 |
| -4 | -15 | 18 | -1.5 | 0 | 1 | -3 | -15 | -11 | -1.5 | 3 | 0.5 |
| -14 | 8 | 17 | 0.5 | 2.5 | 1.5 | 1 | -9 | 6 | 1.5 | 3.5 | 1.5 |
| 16 | 1 | -17 | -1.5 | 0.5 | 0 | -2 | -15 | 13 | -1 | 3 | -1.5 |
| -6 | -14 | 3 | 0 | 0 | 0 | 11 | -7 | 5 | 1 | -1 | 1.5 |
| -2 | -1 | 9 | -1 | 0 | -0.5 | 13 | 15 | 15 | 2 | 3.5 | 2.5 |
| -18 | -15 | 4 | -1.5 | 0.5 | 0 | -2 | 11 | -10 | 2.5 | 1 | -2 |
| 16 | -2 | -20 | 1.5 | 4 | -1 | 1 | -14 | 7 | 0.5 | -3 | -2 |
| -4 | 12 | 0 | 2.5 | -1.5 | -1 | 12 | -8 | -9 | 1 | 0 | -2.5 |
| -6 | -9 | -11 | 3 | -2 | 2.5 | -10 | -8 | -7 | 1 | 0 | 1.5 |
| 9 | 3 | 14 | 1 | -3.5 | 1 | 19 | 4 | 14 | -1 | 0 | 1.5 |
| 5 | 6 | 16 | -1.5 | -1.5 | 2 | -18 | 5 | -3 | -2 | 3 | -0.5 |
| 7 | 4 | -5 | 3 | -2 | 2 | 13 | -3 | 6 | 0.5 | -2 | 0.5 |
| -8 | 20 | 15 | -1.5 | -2 | -2 | 15 | -9 | 15 | -2.5 | -3 | 1 |
| 14 | 11 | 9 | 0 | -1.5 | -1 | -2 | 4 | 17 | 1.5 | -1.5 | -1 |
| 1 | 5 | 11 | 2 | 1.5 | 2 | -14 | -11 | 19 | 1.5 | 0.5 | 1.5 |
| -2 | 0 | 3 | -2 | 3.5 | -2.5 | 10 | 12 | -15 | -2.5 | -2.5 | 0 |
| 14 | 14 | -5 | 2 | 0 | -2 | 3 | -4 | -15 | 0 | 2 | 0.5 |
| -19 | 4 | 10 | 3 | -3 | -1.5 | -9 | -1 | 13 | 2.5 | -3.5 | 1 |
| 17 | -15 | -3 | -3 | -4 | 2 | 9 | 5 | -19 | -1 | -2 | -2 |
| -17 | 3 | -17 | -2.5 | -0.5 | -1 | 14 | -9 | 7 | -1 | 2.5 | 0 |
| 7 | -11 | -18 | 1.5 | 3.5 | 1 | -10 | 15 | -1 | 0.5 | 3 | 0.5 |
| 15 | -5 | -15 | 1 | 2 | 1.5 | 0 | -16 | -12 | 1.5 | 2 | 1 |

Figure 10(A)

|  | Detection Error vs. Random Known Offset | | | | | | Offset after Robotic Correction vs. Random Known Offset | | | | | |
|---|---|---|---|---|---|---|---|---|---|---|---|---|
|  | VERT | LONG | LAT | YAW | ROLL | PITCH | VERT | LONG | LAT | YAW | ROLL | PITCH |
| No. of Data | 50 | 50 | 50 | 50 | 50 | 50 | 50 | 50 | 50 | 50 | 50 | 50 |
| Max+ | 1.07 | 1.95 | 1.57 | 0.94 | 0.85 | 1.2 | 1.43 | 0.73 | 0.6 | 1.14 | 1.51 | 0.82 |
| Beyond +1mm or +1° | 1 | 2 | 2 | 0 | 0 | 1 | 3 | 0 | 0 | 1 | 9 | 0 |
| Max- | -0.97 | -1.07 | -1.62 | -0.81 | -0.97 | -1.03 | -0.95 | -0.97 | -1.34 | -1.12 | -0.53 | -0.92 |
| Beyond -1mm or -1° | 0 | 1 | 3 | 0 | 0 | 1 | 0 | 0 | 3 | 1 | 0 | 0 |
| Mean | -0.15 | 0.11 | 0 | -0.02 | -0.15 | 0.16 | 0.09 | 0.03 | 0.33 | 0 | 0.58 | 0.08 |
| SD | 0.45 | 0.55 | 0.6 | 0.39 | 0.36 | 0.47 | 0.51 | 0.34 | 0.44 | 0.44 | 0.46 | 0.41 |
| Correlation | 0.21 | 0.05 | -0.12 | -0.33 | -0.08 | -0.25 | 0.01 | 0.19 | -0.15 | 0.04 | 0.12 | 0.39 |

Within ± 1mm Detection: 94%  
Within ± 1° Detection: 98.7%  
Within ± 1mm Correction: 96%  
Within ± 1° Correction: 92.7%

Figure 10(B)

Offset after Robotic Correction Vs Random Known Offset

|  | VERT | LONG | LAT | YAW | ROLL | PITCH |
|---|---|---|---|---|---|---|
| No. of Data | 50 | 50 | 50 | 50 | 50 | 50 |
| Mean | 0.09 | 0.03 | -0.33 | 0 | 0.58 | 0.08 |
| SD | 0.51 | 0.34 | 0.44 | 0.44 | 0.46 | 0.41 |

Neutral Config Detection

|  | VERT | LONG | LAT | YAW | ROLL | PITCH |
|---|---|---|---|---|---|---|
| No. of Data | 20 | 20 | 20 | 20 | 20 | 20 |
| Mean | 0.08 | -0.06 | 0.34 | 0.08 | -0.56 | -0.17 |
| SD | 0.26 | 0.18 | 0.34 | 0.29 | 0.18 | 0.29 |

COMPOUND 6D-OFFSET SIMULATING PHANTOM AND QUALITY ASSURANCE PROGRAM FOR PRECISION IMAGE-GUIDED RADIOTHERAPY AND RADIOSURGERY

REFERENCE TO RELATED APPLICATIONS

This application claims the priority benefit of U.S. provisional patent application 61/671,582, filed Jun. 13, 2012. The priority application is hereby incorporated herein by reference in its entirety for all purposes.

FIELD OF THE INVENTION

The invention relates generally to the field of medical devices and their quality assurance. More specifically, it provides a phantom reference object with embedded markers for checking the components of a system used for image-guided diagnostics or treatment.

BACKGROUND

Image-guided radiation therapy (IGRT) is a form of radiation therapy that comprises frequent three-dimensional imaging while the radiation treatment is under way. Concurrent images are compared with imaging done before treatment to map targets and organs within the patient and plan radiation therapy. IGRT relies directly on the imaging modalities from planning as the reference coordinates for localizing the patient. For example, IGRT can combine localization of a real-time cone-beam computed tomography dataset with the computed tomography (CT) dataset used in planning.

On-line adjustments to patient and beam position are typically made during the treatment process, based on continuously updated information throughout the procedure. For example, gold markers may be implanted around the tumor to provide a surrogate position of the tumor. Prior to each day's treatment, imaging system results are returned. If the center of the mass has moved greater than a pre-defined tolerance (for example, 3 mm), then the couch is readjusted and a subsequent reference image is created.

For further information, the reader is referred to the following publications. Cossmann, PH, Eur. Oncol Rev. (2005) provides a general review of advances in IGRT. Jaffray, D A, et al. showed how X-ray imaging could be used for verification and localization in radiation therapy. Modern Technology of Radiation Oncology. Madison, Wis.: Medical Physics Pub (1999). Dawson, L A et al. Lancet Oncol. 7:848-858 (2006) discusses the rationale, benefits, and limitations of IGRT.

SUMMARY OF THE INVENTION

This invention provides a device for checking the performance of an image-guided radiation therapy (IGRT) apparatus. The device (referred to here as a phantom) has a central body with detectable markers, rotatably suspended on a ball joint so that the pitch, roll, and yaw may be adjusted. The body is secured against a base plate, which in turn may be positioned laterally, longitudinally, and vertically within the patient treatment area. Thus, the phantom can be adjusted through six degrees of freedom so as to simulate patient positioning. To perform quality control, the phantom is secured at a predetermined offset, and the position is detected by the IGRT apparatus. The robotic couch is then allowed to compensate, a second measurement is made. The measured values are compared with the predetermined offset to assess both the accuracy in detecting the position of the phantom, and the accuracy of the mechanical correction.

A particular aspect of the invention is a quality assurance device for checking a robotic couch control system. The couch may be part of any positioning device for use in the manipulation of a human or mammalian subject or other object in any context—for example, and without implying any limitation, for the purpose of detection, diagnostics, therapy, manufacture, or in the positioning of heavy equipment. By way of illustration, the robotic couch control system may include a robotic couch, a detecting apparatus for determining the position of an object on the robotic couch, and a microprocessor programmed to control the robotic couch according to its position as measured by the detecting apparatus.

The device typically comprises a body configured for disposing on the robotic couch, and detectable markers affixed on or within the body. Each marker is configured so that its position may be determined by the detecting apparatus when the device is disposed on the robotic couch. The device also has a means for adjusting and securing the pitch, roll, and yaw of the body in relation to the robotic couch when the body is disposed on the robotic couch.

The device of this invention can be used for quality assurance (QA) of equipment configured for IGRT of a patient supported or secured upon the couch. The IGRT apparatus may be operated to determine the position of the body by way of a suitable detection means, such as computer guided tomography (CT). The body of the device may be secured to the robotic couch by way of a base plate with projections or extensions that are in direct contact with the couch. Detection markers or reference points in the device may be rods or ball bearings, each configured so that the detecting apparatus can determine the position of the body of the device. The device may also be adapted with infrared spheres for servo-tracking of adjustments of the robotic couch in real time.

By way of example, the device may have a body with detectable markers suspended above the robotic couch by way of a ball joint. The ball joint may be mounted on a supporting rod disposed upon a base plate that is configured for placing securely upon the robotic couch. Pitch, roll, and yaw of the body of the device in relation to the robotic couch may all be adjusted by pivoting the body on the ball joint. Once adjusted, the body can be held in place by way of a securing means, such as a plurality of vertically positioned support screws. The screws may be oriented to pass downwards from the body towards a base plate through a lateral support structure projecting from the body. The body of the device may be adjusted and secured within a suitable range in accordance with normal operating parameters when in use for therapy. The device may also have a built-in grid for aligning and adjusting the device horizontally or 3-dimensionally on the robotic couch using the cross-hair projection of the IGRT apparatus.

Another aspect of the invention is a calibration system comprising various components of the invention, assembled together as a kit during manufacture for sale as a kit, or assembled together by the user from components acquired separately. For example, the kit may contain a device of this invention, plus one or more inclinometers for determining, calibrating, and/or adjusting the pitch and roll of the body in relation to the robotic couch. Two inclinometers that are separate and apart from the body of the device can be secured orthogonally in relation to each other—for example, using a tray adapted to receive the base or lower surface of each inclinometer and secure them in mutually orthogonal positions. The tray with the inclinometers can then be placed upon the body of the device and secured in place so that the pitch, roll and yaw of the offset may be determined and adjusted accurately.

A quality assurance system, device, or kit of this invention may also have a microprocessor programmed to obtain and compile 6-dimensional data with respect to change in position of the body of the device upon the robotic couch in relation to a previous position, as measured by the detecting device. Such information can be obtained before the robotic couch control system makes adjustments to the position of the robotic couch to compensate for the change in position. Alternatively or in addition, the position of the device may be ascertained while in operation, after the robotic couch control system makes adjustments to the position of the robotic couch. Typically, a microprocessor operatively connected to the device and/or the IGRT apparatus is programmed to compile information from multiple changes in position of the body of the device in relation to the robotic couch over an appropriate range in relation to the original position.

Another aspect of the invention is an IGRT apparatus having a device as already referred to positioned upon the robotic couch.

Further aspects of the invention include several methods for quality assurance (QA) of an IGRT apparatus. For QA of the detection and data processing function of an IGRT apparatus, the method may comprise the steps of securing the device as already outlined upon the couch at an original position; operating the IGRT apparatus so that it determines the 6-D position of the device at the original position; repositioning and securing the device upon the couch at a new 6-D position; operating the IGRT apparatus so that it determines changes in the position of the device at the new position; and then determining and recording changes in the pitch, roll, yaw, and horizontal position of the device in relation to the original position. The changes determined by the IGRT apparatus are then compared with the changes determined independently of the IGRT apparatus as already outlined.

For QA of the patient repositioning function of an IGRT, the method typically comprises the steps of securing the device upon the couch at an original position; operating the IGRT apparatus so that it determines the position of the device at the original position; repositioning and securing the device upon the couch at a new position; and then operating the IGRT apparatus so that it adjusts the position of the robotic couch to compensate for changes in the pitch, roll, yaw, and optionally the horizontal position of the device at the new position in relation to the original position. The pitch, roll, yaw, and horizontal position of the device at the new position is then determined Ideally, the markers in the device will be placed back in the position before creating the offset and allowing the robotic couch to compensate. Deviations from the original position after readjustment indicate an error in marker detection, or in servo control of the robotic couch.

The steps in any of these QA methods are repeated iteratively over a predetermined range of each of the positional indicators so as to obtain sufficient data for a robust statistical analysis and determination of any errors in detection, calibration, or operation. The QA methods may also have a step for determining whether data obtained from the IGRT apparatus according to the method is within acceptable operating parameters. The methods may be used for confirming proper installation of a new IGRT apparatus; or for quality control conducted on a periodic basis after an IGRT apparatus has been installed.

Another aspect of the invention is a method for repairing an IGRT apparatus. This typically comprises calibrating the IGRT apparatus; and then adjusting the IGRT apparatus to reduce changes determined by the IGRT apparatus in relation to changes determined independently of the IGRT apparatus.

A further aspect of the invention is a method of irradiation, excision, or other treatment if a subject in need thereof. A treatment apparatus such as an IGRT is calibrated or adjusted according to the methods of the invention, and then used to irradiate or otherwise treat the subject so as to impact the target area while avoiding radiation-sensitive areas where the clinician wishes to avoid adverse effects of the treatment apparatus and methods.

Other embodiments of the invention will be apparent from the description that follows.

DESCRIPTION OF THE DRAWINGS

FIGS. 2(A) and (B) are a transverse section through the pane of the tumor; FIGS. 2(C) and 2(D) are the sagittal and coronal sections, respectively.

FIG. 4(B) is a cross-section through the center of the device; FIG. 4(A) is a display of both longitudinal and lateral cross-sections set at a diagonal.

FIG. 7 is a table of pre-determined random target offsets that generated for quality assurance testing of an IGRT apparatus using the phantom device of this invention.

FIGS. 10(A) and 10(B) provide compilation analysis of 50 sets of data for assessing detection error correction error respectively. In this example, there were systematic mismatches between neutral configuration at the LINAC™ that measured by CT due to an error at the neutral configuration detection.

DETAILED DESCRIPTION

Overview

Figure 1:
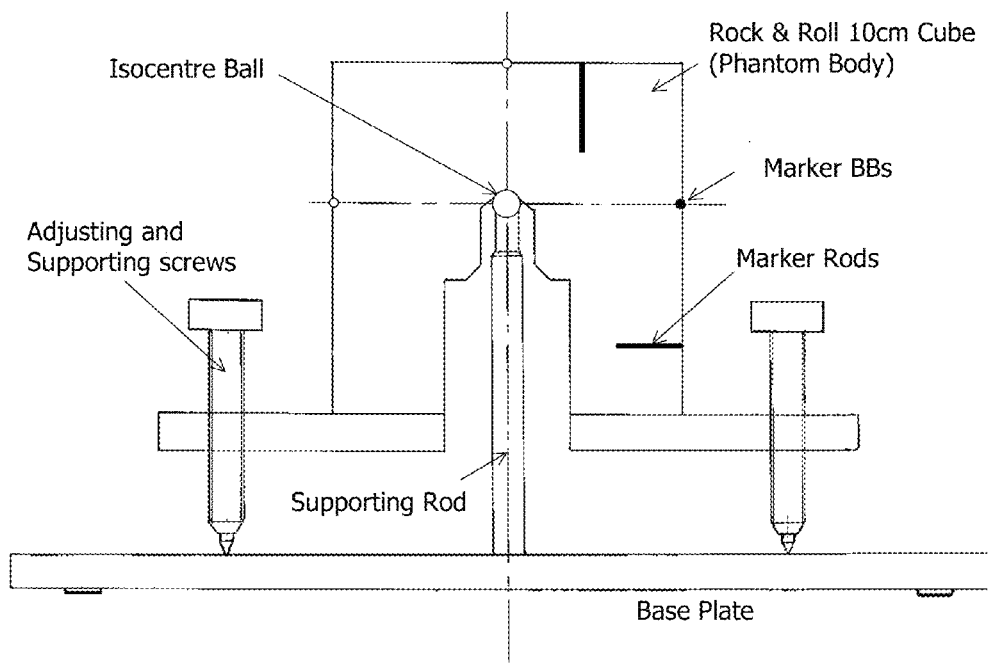
FIG. 1 is a cross-sectional view illustrating a phantom device of this invention. It comprises a body with detectable markers, the body being rotatably suspended on a ball joint mounted on a supporting rod. The pitch (forward to backward tilt), the roll (the side to side tilt), and the yaw (rotation of the body on the horizontal plane) may be altered by pivoting about the ball joint, and then secured in position by way of the support screws.

Deviations in accuracy of an image-guided radiation therapy (IGRT) apparatus can endanger radiation-sensitive tissues that neighbor the target tissue in a patient undergoing treatment. This invention provides products and methods to detect such errors. A quality assurance device of this invention is secured upon the robotic couch at a predetermined offset. The offset is measured by the IGRT apparatus, which then readjusts the robotic couch to compensate. Both the measured offset and the readjustment are compared with the predetermined offset to assess the accuracy of the IGRT apparatus. The quality assurance systems of this invention can be used to assess and reconfigure the apparatus, thereby ensuring its accuracy and clinical effectiveness.

Technical Context

Radiation Therapy (RT) is a form of clinical medicine that uses ionizing radiations to treat target lesions—such as a tumor. An external beam RT machine (Medical Linear Accelerator or LINAC™) generates and directs radiation to the lesion from one meter away. The quality of External Beam RT (Teletherapy) corresponds to the accuracies in dosimetry and in target positioning.

Image-Guided Radiation Therapy (IGRT) is an advanced form of RT developed to achieve high accuracy in target positioning. The IGRT principle is to determine the position of the target tissue inside the patient while undergoing treatment (for example, using diagnostic X-ray). The patient is secured upon a robotic couch. Error of positioning is determined, and then corrected by moving the patient back to the reference position using the robotic couch. IGRT enables the clinician to treat the target tissue while avoiding radiation sensitive tissues that may be nearby. IGRT is especially effective in treatment protocols requiring high precision: for example, head and neck cancer, or tumors near the spinal cord where the target is very close to those radiation-sensitive critical structures or Organs At Risk (OAR).

The reference position is obtained from the patient's CT images previously obtained during planning of the treatment. Such plans typically have a main CT image set, on which the dosimetry and all the geometrical factors of the treatment are based. Alternatively or in addition, real-time CT images of the target are obtained and compared with a reference. Sophisticated detection means and computer algorithms have been developed to determine and asses slight differences between the two sets of images. Correction for the 6D setup errors is then done under control of the IGRT apparatus by way of the robotic couch.

The radiation dose administered in RT is limited by the potential exposure of neighboring organs at risk. Because of the precision of the IGRT apparatus, the target margin can be reduced so as to irradiate essentially the entire tumor, while minimizing exposure of neighboring tissues. If the treatment is accurate enough spatially, it is possible to escalate the prescribed radiation dose to a more effective level. Modern IGRT apparatus have a precision of detection, readjustment, and treatment of that can match or exceed ±1 mm translation and ±1 degree rotation.

Figure 2:
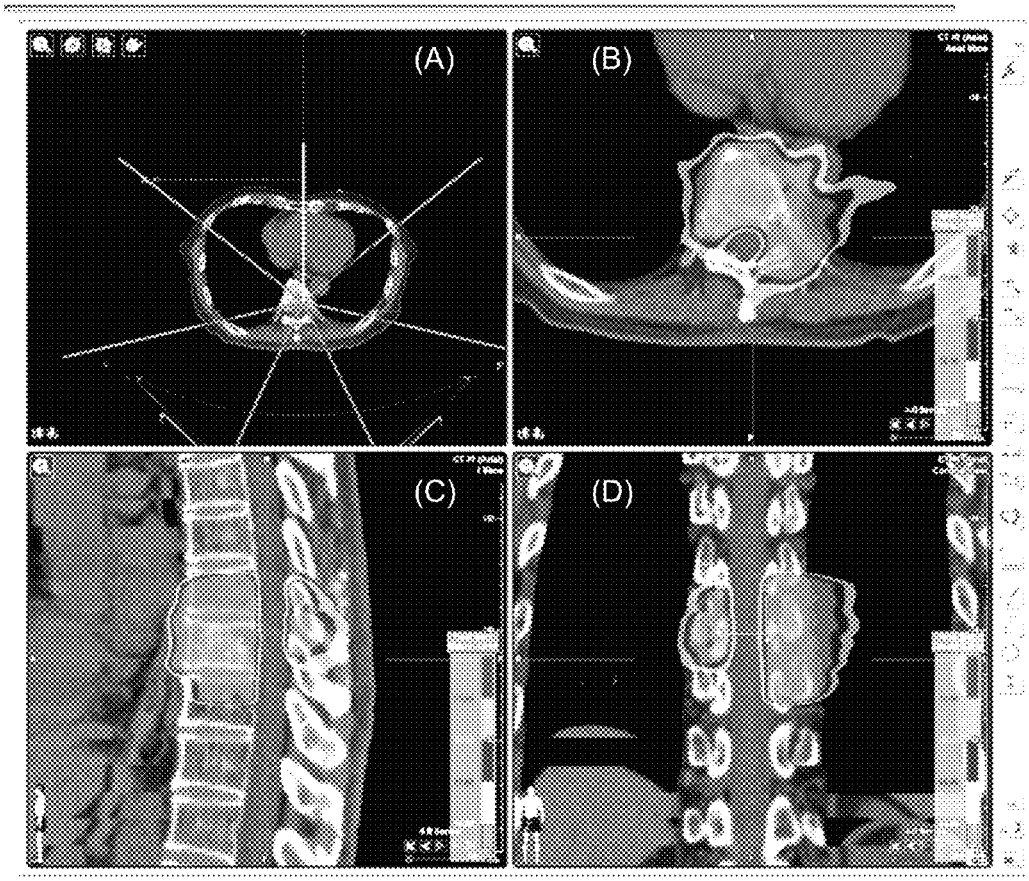
FIG. 2 is a family of CT images showing a tumor targeted for therapy adjacent to the spinal cord which is radiation sensitive.

FIG. 2 is a family of CT images showing a tumor adjacent to the spinal cord of a subject being prepared for image-guided radiotherapy. FIG. 2(A) is a transverse section through the pane of the tumor; FIG. 2(B) is a close-up. FIGS. 2(C) and 2(D) are sagittal and coronal sections, respectively. The tumor is located in about the middle of each image. The object of treatment is to irradiate the tumor mass as close as possible to the margin without compromising the spinal cord.

An IGRT apparatus should routinely be calibrated to ensure that the correct radiation dose is delivered to the patient in the correct location. Overdose can be fatal or induce serious complications, while underdose can lead to the loss of lesion control.

A prototype device of this invention (also referred to as a "phantom" or "6-D phantom") is exemplified below. To calibrate an IGRT apparatus, six dimensional offsets (lateral, longitudinal, vertical, pitch, roll, and yaw) were generated randomly. A robotic couch associated with the IGRT apparatus was manually operated to accommodate the horizontal and vertical offsets. The phantom was then adjusted manually to accommodate the rotational offsets. Differences between the offset measured by the IGRT apparatus and measured independently were compared. Offset of the device may also be set by another device, or by adapting the phantom to be self-actuating by way of servo-control systems.

The Offset Simulating Phantom Device

FIG. 1 is a cross-sectional view illustrating a non-limiting prototype of a phantom reference or device of this invention adapted to simulate compound 6-D offsets to test an IGRT apparatus.

The central component of the device is a body of material that is transparent or translucent to the sensing mechanism the treatment system uses to position the patient to be treated. In this illustration, the body of the phantom is substantially cubical in shape. This facilitates both the manufacture of the device and its alignment during use. However, any shape can be used, providing it has the desired operating parameters. In this illustration, the body is made of polymethyl methacrylate (PMMA). Any form of plastic or other reasonably light and substantially rigid material can be used, providing the material does not interfere with the positioning or repositioning of the device or the data collection.

The body has a means for adjusting and securing the pitch, roll, and yaw of the body in relation to the robotic couch. In this illustration, the body of the phantom pivots about a ball joint located at or near the center of mass of the body. The support portion of the ball joint is mounted on a supporting rod, made of a suitably rigid and weight-bearing material such as aluminum or other metal. The receiver portion of the ball joint is a substantially spherical receiving cup or socket positioned within a cavity in the body that opens and flares downwards to enable a range of positions. The pitch (forward to backward tilt), the roll (the side to side tilt), and the yaw (the rotatory orientation of the body on the horizontal plane) may all be altered by pivoting the receiver portion on the support portion. Other means for adjusting the pitch, roll, and yaw include hinge arrangements, one or more ball and socket joints, and pliable connections that can be used in combination to allow adjustment of the body in terms of its pitch, roll, and yaw in relation to the robotic couch.

In this illustration, the body may be adjusted and secured in its offset position by way of vertically positioned support screws (typically three or four) that project downwards towards a base. In turn, the base rests and is secured upon the robotic couch by way of downward projecting feet, machined to conform in a stable fashion to a flat surface, or within the curvature or other technical features of the robotic couch the device is being used to calibrate. The set screws pass through a lower lip on the body of the phantom, made by permanently joining or fusing the cube component to a horizontal sheet or platform of plastic material (here illustrated as about 1 cm thick), that is both wider and longer than the cube. The horizontal platform is cut away below the cavity housing the socket for the ball joint, so that the support for the ball joint may pass upwards from below to secure the socket. As an alternative to using a ball joint for support, body may be set up for securing with a plurality (such as four) downward projecting set screws or adjustable legs which bear the weight of the body. They are adjusted in pairs front-to-back or side-to-side to the desired roll and pitch. The yaw may be adjusted by moving the device upon the robotic couch around a central vertical axis.

To adjust and secure a phantom offset device as shown in FIG. 1 in a neutral or offset position, the base of the device is positioned on the robotic couch by aligning appropriately with the orientation lines projected from the IGRT apparatus. The robotic couch is adjusted vertically to set the descried vertical position. The body of the phantom is adjusted about the ball joint for the desired pitch, roll, and yaw using the set screws, adjusting the screws so that the weight of the body rests securely on the supported ball of the ball joint. The phantom may also be provided with its own independent elevation system, such as a scissor lift that can be adjusted to the desired vertical position, and two orthogonal horizontally sliding components to adjust the horizontal position independently of the robotic couch.

Figure 3A:
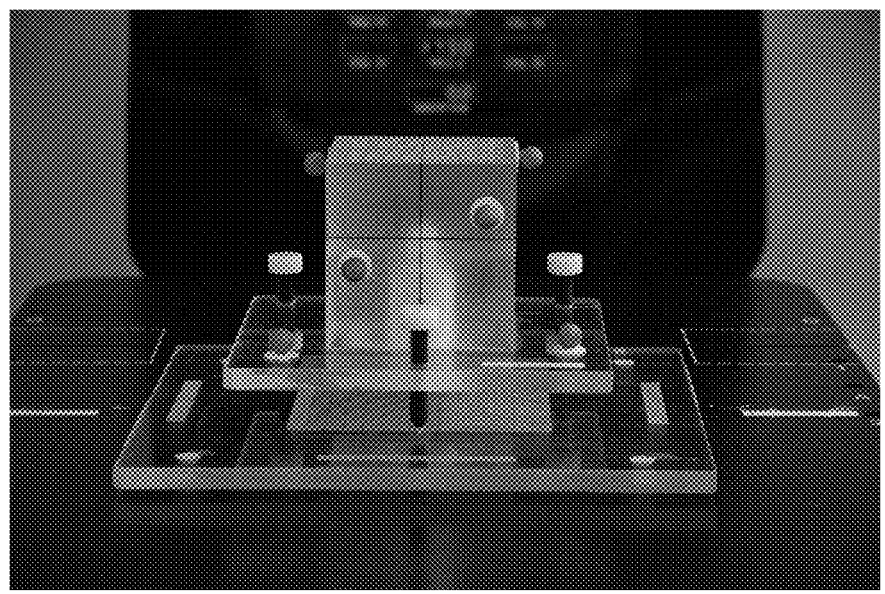
FIG. 3(A) and FIG. 3(B) are elevated views of the phantom device from the front and from the diagonal. The device is secured in position on the robotic couch of an IGRT apparatus.
Figure 3B:
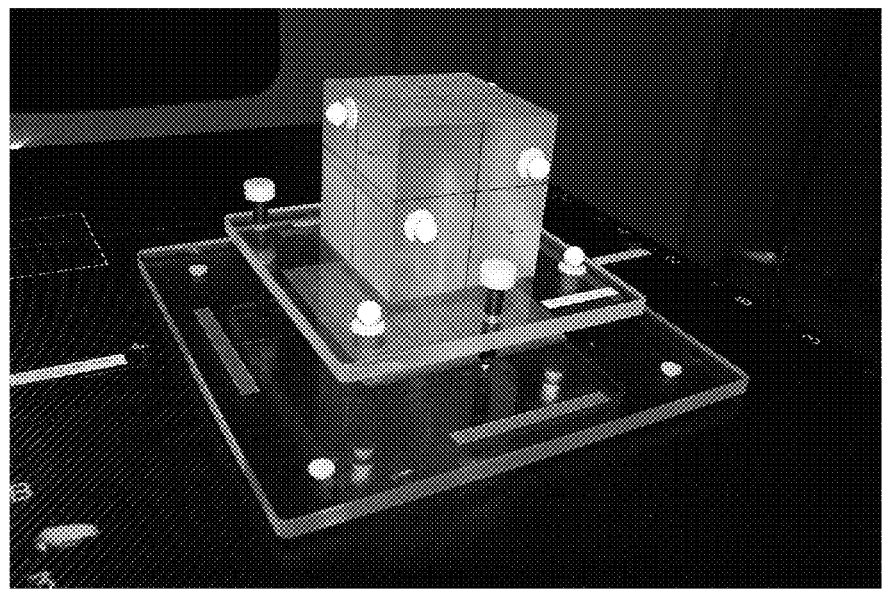

FIG. 3(A) is an elevated view of the prototype device from the front, secured in a neutral position on the robotic couch of an IGRT apparatus. FIG. 3(B) is an elevated view from the front diagonal. Infrared spheres are present as a marker system that the IGRT can use for servo-tracking of automatic adjustments to the robotic couch during operation: there are two on the front face, one on each side, and two on the outer platform.

Figure 4:
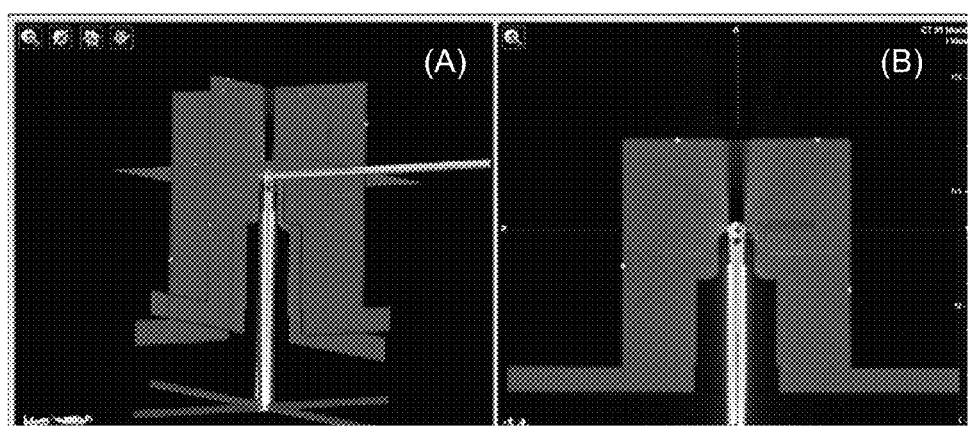
FIG. 4 provides CT images of the body of the phantom offset device resting on the vertical support.

FIGS. 4(A) and 4(B) are CT images of the body of the phantom offset device resting on the vertical support by way of the ball joint at the top of the downward-oriented cavity. FIG. 4(B) is a cross-section through the center of the device; FIG. 4(A) is a display of both longitudinal and lateral cross-sections set at a diagonal.

Figure 5A:
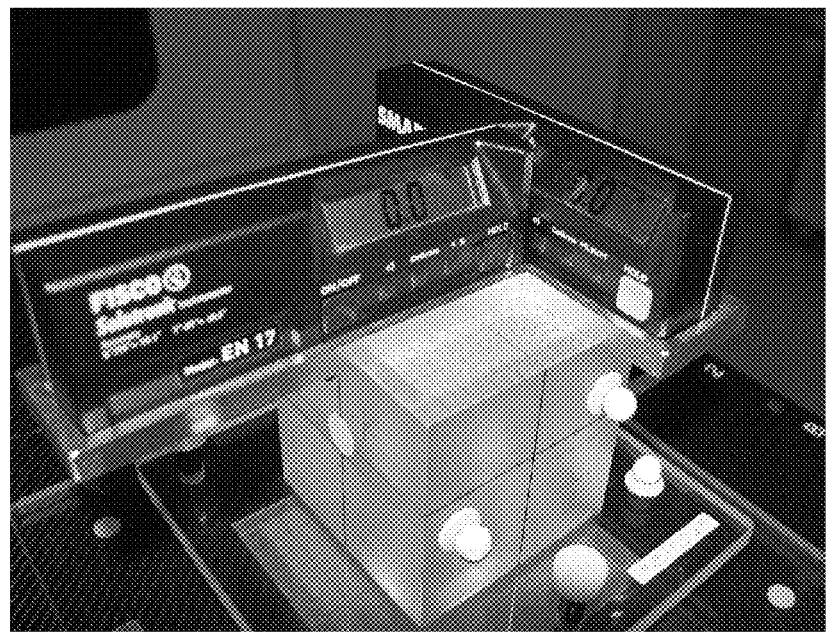
FIG. 5(A) show the phantom offset device being adjusted to a particular pitch and roll using digital inclinometers.

FIG. 5(A) show the phantom offset device being adjusted to a particular pitch and roll using digital inclinometers. There is a tray underneath the inclinometers that is configured on the upper surface with ridges to accommodate the inclinometers securely in mutually orthogonal (90 degree) positions. The tray is also configured with ridges underneath to accommodate the inclinometer assembly in a secure position on top of the body of the phantom device orthogonal to one of the sides. The tray is detachable from the body of the device during measurement and adjustment by the robotic table. The tray is detachable from the inclinometers for convenience of storage. Use of two inclinometers simultaneously allows the pitch and roll to be adjusted at the same time.

Figure 5B:
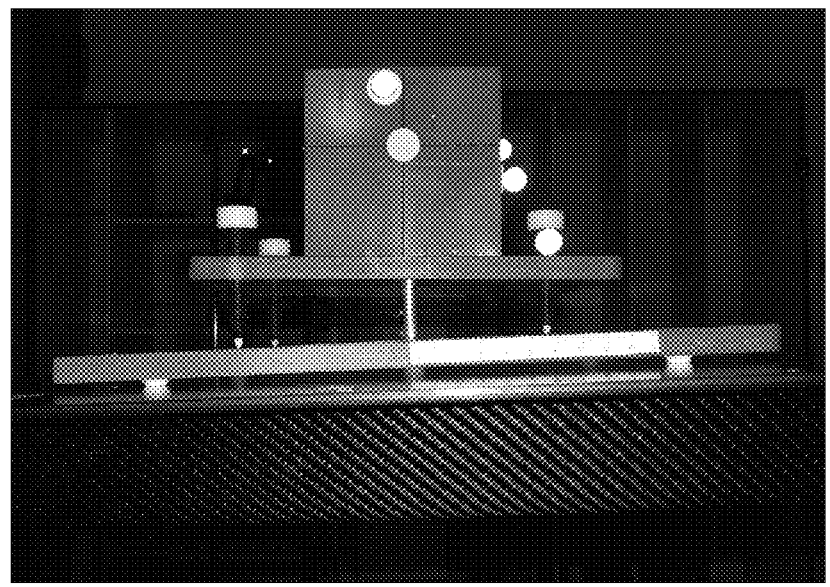
FIG. 5(B) shows the phantom offset device adjusted to a particular pitch, and compensated for the offset after the robotic couch correction

FIG. 5(B) shows the phantom offset device adjusted to a particular pitch. The robotic couch has then been operated by the IGRT apparatus, resulting in a position where the robotic couch is at an angle relative to the horizontal that compensates for the device offset.

Calibration System

The body and securing means of the offset device can be packaged and distributed as a kit with other components useful in the calibration and quality control of IGRT apparatus.

Figure 6:
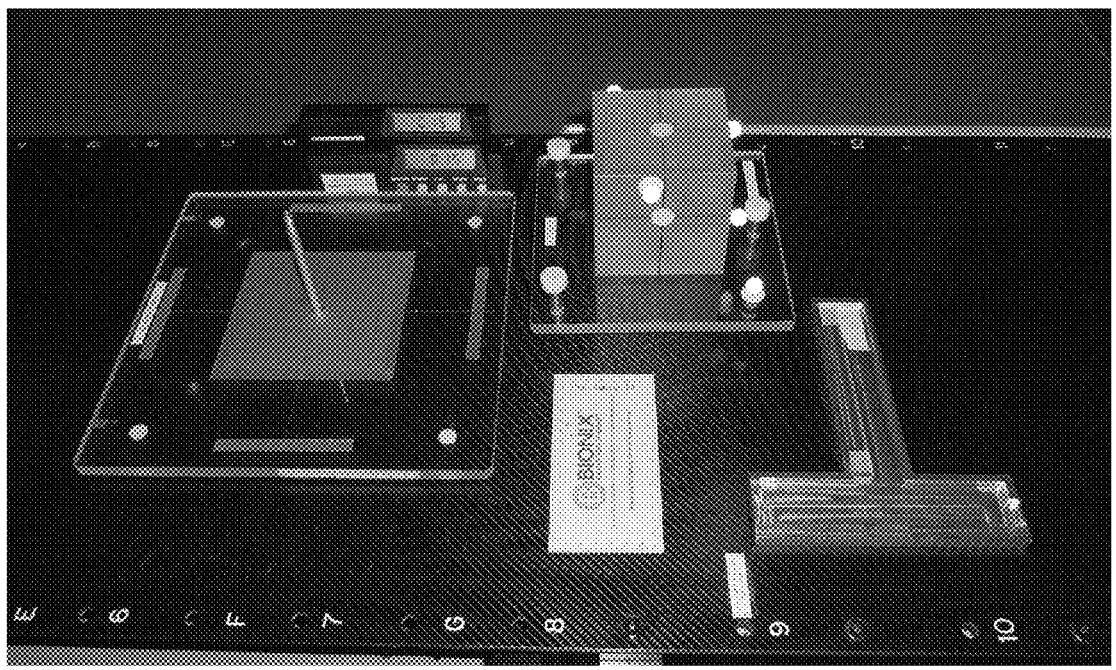
FIG. 6 shows a set of components according to this invention assembled as a kit.

FIG. 6 shows a set of ETRQA components comprising the body and a base with a support sericulture having a ball joint. For ease of alignment, both the base and the top of the body are provided with a marker grid. Optional components are two inclinometers, shown at the back, and the tray for securing to the body of the device in an orthogonal orientation.

The device may also be provided with a microprocessor system to generate random offset positioning data in a quality control exercise. The device may be configured with an input means to determine the 6D position of the device in relation to the couch or the IGRT apparatus, and a microprocessor and computer storage system to process the determined position. The microprocessor may be programmed to obtain and compile information regarding a change in position of the body of the device upon the robotic couch in relation to a previous position, as measured by the detecting device. The microprocessor may be programmed to obtain and compile information regarding a change in position of the robotic couch and/or the device as a result of operating the IGRT to compensate for an offset of the phantom device. The microprocessor may also be programmed to adjust the pitch, roll, and yaw of the body of the device by way of internal servo control mechanisms, in accordance with predetermined or calculated random offset positioning data.

Quality Assurance Program

To use the phantom offset device of this invention in a calibration or QA program, the device is secured to the robotic couch to define a neutral or starting position. The device is then readjusted with particular predetermined or random offset positional data, and the IGRT apparatus is tested to see if it can recognize and/or compensate for the changed position.

The offset positional data can be defined according to a predetermined schedule designed to test the range of operation of a particular IGRT or family of such treatment systems. Alternately, the preset positional data can be generated randomly ad hoc to prevent the operator from gaming the test. Typically, at least 10, 20, or 50 sets of offset data are applied to the phantom, and then the response of the IGRT is determined A typical test range may include a range wherein the horizontal and/or the vertical position of the device is changed by at least 10, 25, or 100 mm in any direction; and the pitch and roll are changed by at least 2 or 5 degrees from the original position.

Once the phantom has been positioned with the intended offset, the IGRT may be operated so as to make its own determination of changes in the pitch, roll, yaw, and optionally the horizontal and/or the vertical (i.e., 6-D) positions. The changes determined by the IGRT system are then compared with the changes calculated independently in view of the actual offset. The IGRT may also be operated to compensate for the offset, in which case the pitch, roll, yaw, and optionally the horizontal and/or the vertical 6-D positions are measured in relation to the original position.

The user can then determine whether data obtained from the IGRT apparatus according to the method is within acceptable operating parameters. Quality assurance (QA) can be done confirming proper installation of an IGRT apparatus when first commissioned. Quality assurance can also be done as part of a regular, periodic, or regulatory reassessment of the IGRT once put into clinical use. In the event that the IGRT system is found unable to adequately detect and/or adjust for an offset in any of the six degrees of freedom, the IGRT apparatus may be repaired or reengineered to improve performance, and then retested using the devices and calibration methods of this invention.

Clinical Use

This invention also provides a method of image-guided radiation treatment in a subject. The IGRT apparatus is calibrated, verified, or adjusted using the products and methods of this invention. The IGRT apparatus is then operated to perform the image-guided radiation treatment on the subject, according to proper operating procedures of the IGRT apparatus and proper standards of clinical practice.

The invention has been illustrated in this disclosure using a particular IGRT apparatus: namely, the ExacTrac™ model made by BrainLAB, Germany. Any clinical method that involves image-guided therapy of any kind using sensor based robotic adjustment of the patient's position may be calibrated using the devices and methods of this invention.

Types of therapy include linear accelerator (LINAC) based therapy, generating X-rays in the 6 MV range, Gamma Knife therapy, generating gamma rays from decay of $^{60}Co$ proton beam therapy (PBT) using protons produced by a medical synchrotron, ultrasound surgery, and high precision robotic therapy. Real-time imaging systems include computed tomography (CT), fluoroscopy, digital X-ray, cone beam, MVCT (megavoltage computed tomography), MRI, and optical and infrared tracking.

Therapy may be planned in advance by imaging the patient, determining regions to be irradiated or excised, and regions to be avoided. The patient is then placed on the robotic couch, which is operated so as to treat the target regions and avoid other tissues, particularly those that would be adversely affected by irradiation or excision. Reference markers positioned on or around the patient are identified, and used to guide operation of the robotic couch. Alternatively or in addition, the patient may be imaged during the course of therapy to identify locations of target regions and regions to be avoided and/or to confirm the location of these regions after operation of the robotic couch in accordance with an image taken before treatment or earlier during the treatment protocol.

Glossary

The terms "3D", "5D", and "6D" mean three, five, and six degrees of freedom, respectively, with respect to a particular calculation or usage. "5D" in reference to position of an object refers to its horizontal and rotational positions, as defined below. "6D" is the position of the object also including its vertical position.

"Image-guided radiotherapy" or "IGRT" means any type of therapy (including but not limited to surgery or radiation) that comprises applying one or more forms of radiation to a patient for purposes of therapy (not just imaging, diagnosis, or detection), and is guided in its activity or location by periodic concurrent imaging of the treatment area in the subject being treated.

The term "phantom" as used in this disclosure generally refers to a device of this invention. It is a physical object devised to simulate the position of a human body, in part or in full. Unless stated otherwise, there is no required nexus with the opera house in Paris.

Each device, apparatus, or system of this invention has a plurality of components that are structurally and functionally related in the manner specified. Components may be separate from each other, or may interact physically when placed adjacent or upon each other.

The term "body" used in relation to a device, apparatus, system, or method according to this invention is an inanimate structure having the specified attributes. There are no particular requirements for the shape or size of the body unless specified. Preferred shapes have one or more sharp edges to facilitate alignment, and other adaptations to facilitate handling and usage.

The term "calibrating" means a process by which data is collected in relation to operation of a device, apparatus, or system for any purpose.

A "robotic couch" is an apparatus configured to support or restrain a mammalian subject in a comfortable and stationary position (typically a lying position). No particular shape or orientation is necessarily implied. The 6-D couch is configured so that it may be mechanically operated to adjust its pitch, roll, and yaw, its horizontal position in either dimension, and often its vertical position, typically under control of a microprocessor.

A "microprocessor" is any data processing device (typically a computer) of specific or general application that has been configured or programmed to cause operation of a device or apparatus, or to process or compile data in the manner indicated.

The term "detecting apparatus" as used in this disclosure means an apparatus that has been configured to detect the position of a three-dimensional object in at least three of the six degrees of freedom.

The "position" of a three-dimensional object, such as a device, device component, apparatus, or subject generally refers to the position of the object in relation to a fixed frame of reference (such as a room in which an IGRT apparatus is installed). The position comprises the location of the center of mass in three-dimensional space, plus its pitch, roll, and yaw compared with some neutral or starting position. The "position" of an object measured by a detection apparatus may comprise any three, four, five, or all six of these parameters, depending on the capabilities of the detection.

Horizontal position is the position of an object in both horizontal dimensions: longitude and latitude or forward to back and left to right in relation to a frame of reference, such as a room or a device component. Vertical position is the position of an object vertically in relation to the ground or floor. The rotational position is the pitch, roll and yaw of the object about an internal reference point, such as its center of gravity or a supporting ball joint.

Physical objects are "secured" when they are in a position that is reliably unchanging in the absence of it being caused to move by a human subject, another device or device component, or an act of God. A physical object is secured when it is supported structurally at a plurality of locations from below, even when it is not tethered, clasped, or bonded to the supporting structures or another object (such means of securing being optional).

A "ball joint" of a device of this invention is a connection between two components in which one component presents a ball, and another object presents a receiver that is configured to conform to the ball so that the second component may pivot in relation to the ball both forwards and backwards (the "pitch"), side to side (the "roll"), and rotationally about the ball (the "yaw").

"Acceptable operating parameters" when used in reference to detection apparatus or robotic couch of an IGRT apparatus are a range with respect to the data determined by the detection apparatus in relation to an external measurement is acceptable according to regulatory requirements or locally defined standards.

"Proper installation" or "proper maintenance" of an IGRT apparatus is confirmed when data obtained from the detection apparatus and by independent measurement fall within acceptable operating parameters.

EXAMPLE

This section demonstrates calibration and quality assurance of the ExacTrac™ (ETx) model IGRT apparatus using the products and methods of this invention.

A phantom reference device to simulate compound 6-D offsets in an IGRT apparatus was constructed from PMMA as designed in FIG. 1 and illustrated in FIGS. 3 to 6.

FIG. 7 is a table of pre-determined random target offsets that was generated for quality assurance of an ETx. For each consecutive measurement point, the device was set to the 6D location of each consecutive row in the table.

Remove the Rocking Phantom (the body of the device) from the ball joint
Orientate the base to the Lasers and Cross-hairs using the grids incorporated in the device
Adjust the VERT (vertical position)
Adjust the LONG and LAT (longitude and latitude)
Replace the Rocking Phantom
Set Inclinometers on the Phantom
Adjust the PITCH roughly by rotating the body about the ball joint and turning the support screws accordingly
Adjust the ROLL in the same fashion
Fine adjust PITCH and ROLL (Make sure not to lift the Phantom)
Turn LINAC™ Coll to the Yaw angle
Adjust the YAW to the Cross-hairs by LINAC Ang
Final check (Inclinometers should align with lasers, not the phantom)

Fifty sets of data (position adjustments and measurements) were typically used annually for a routine ETRQA program.

Figure 8A:
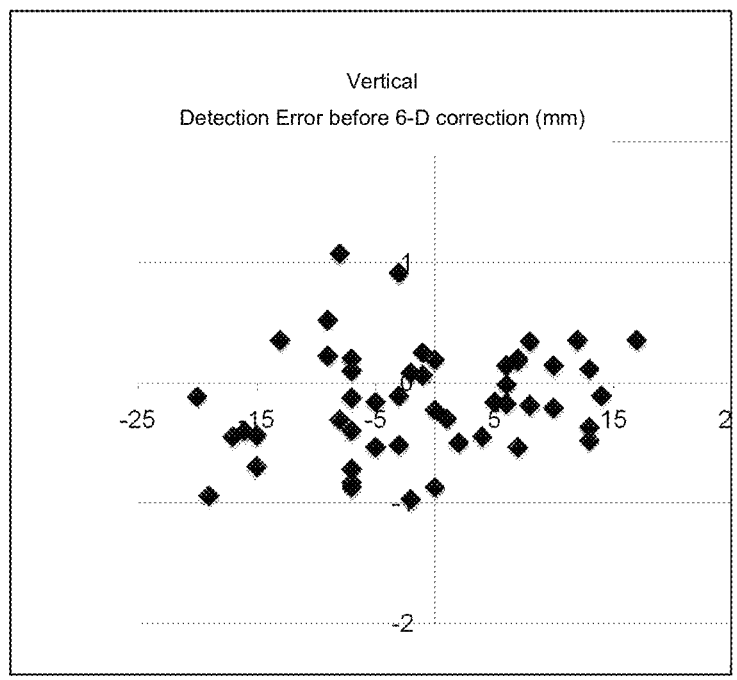
FIGS. 8(A) and 8(B) shows use of the phantom device for determining detection error in the VERT (vertical) and ROLL dimensions.
Figure 8B:
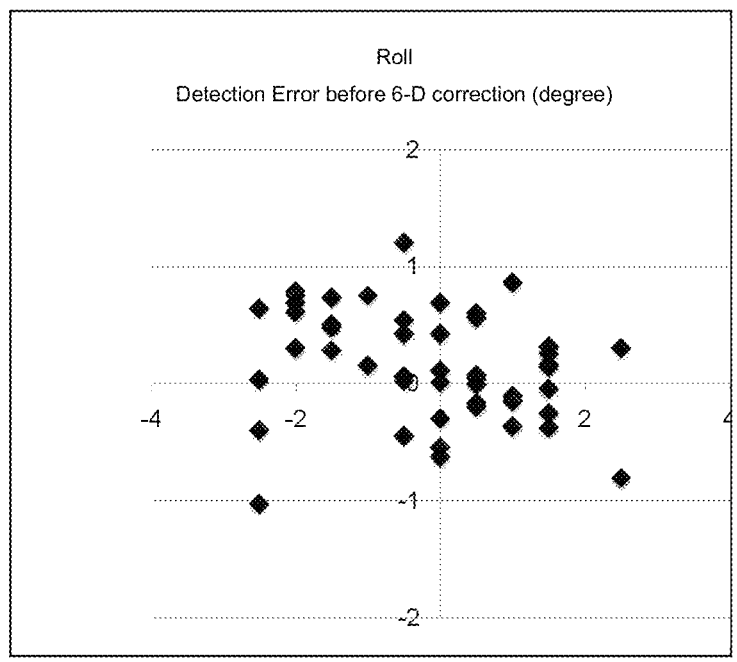
Figure 9A:
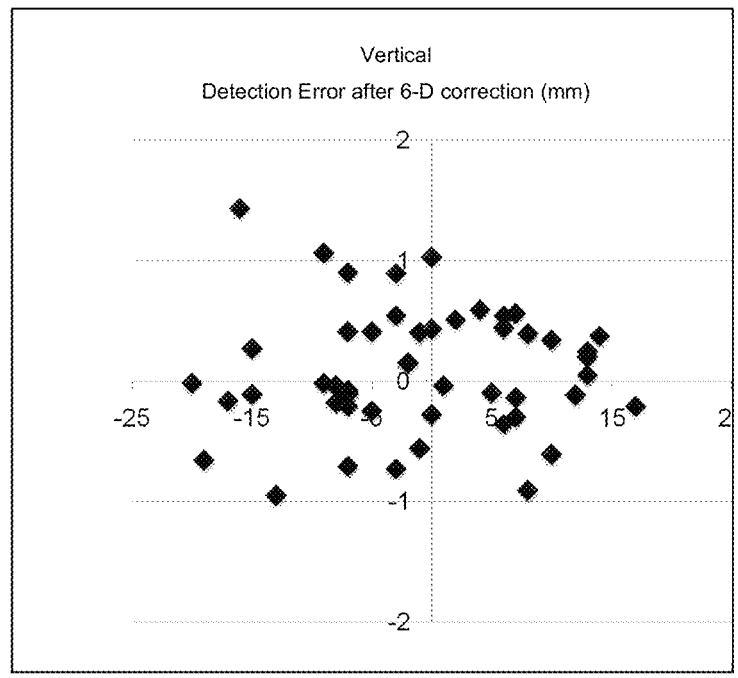
FIGS. 9(A), 9(B), 9(C), 9(D), 9(E), and 9(F) show use of the phantom device for determining adjustment error in the VERT (vertical) LONG (longitude) LAT (latitude) YAW ROLL PITCH dimensions respectively.
Figure 9B:
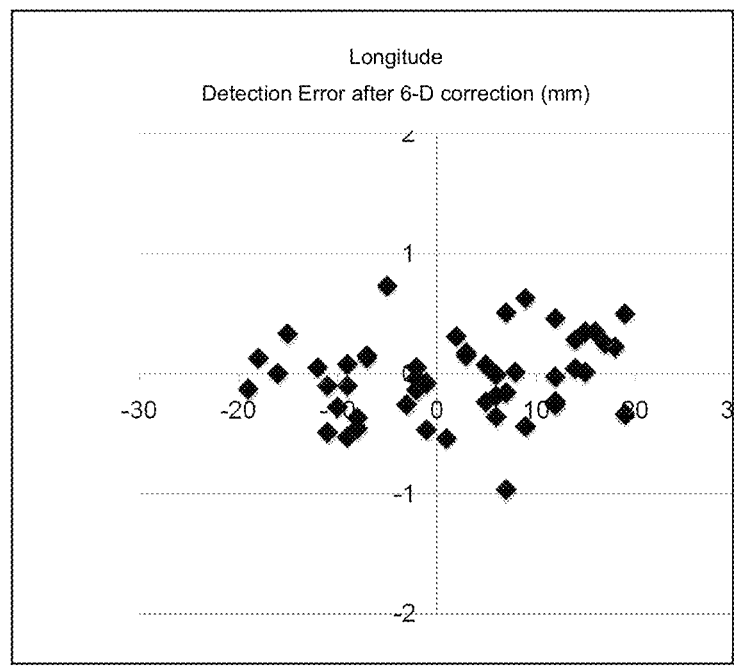
Figure 9C:
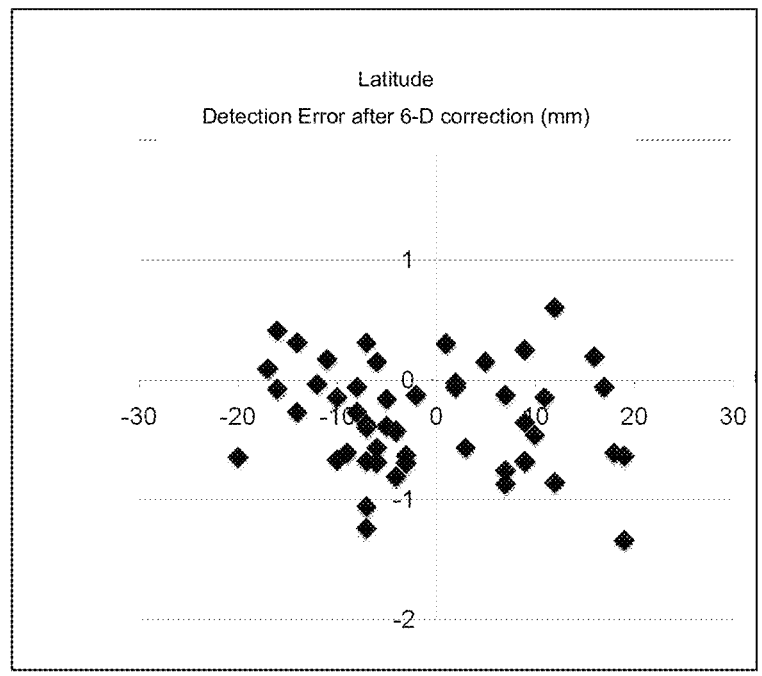
Figure 9D:
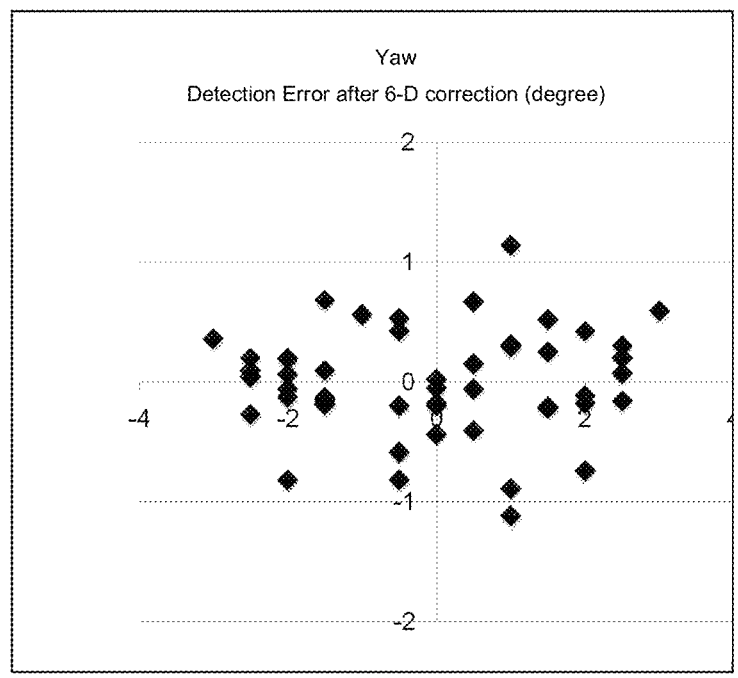
Figure 9E:
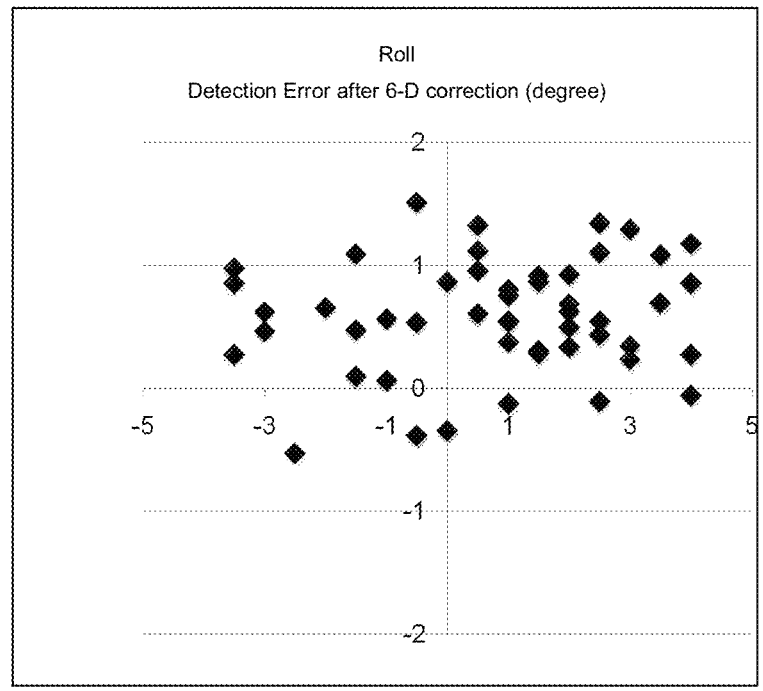
Figure 9F:
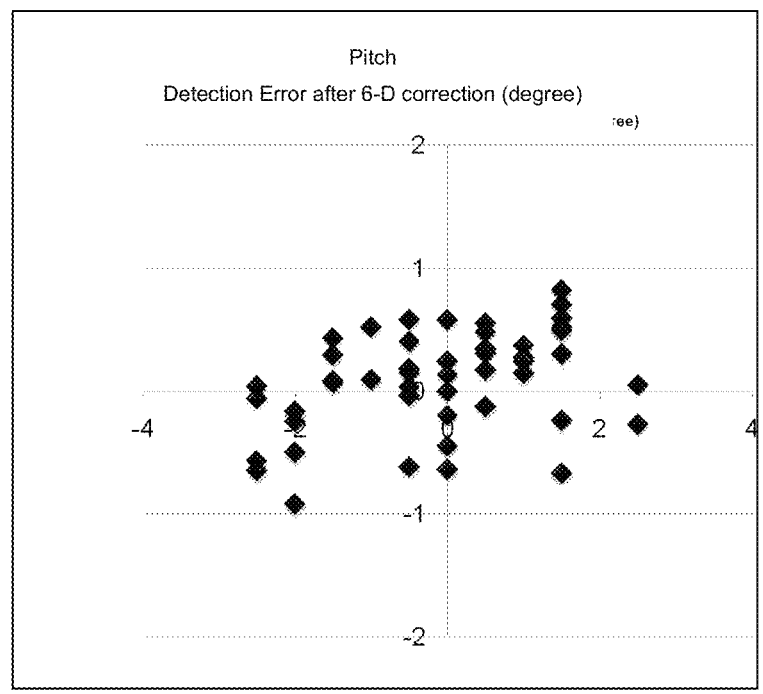

FIGS. 8(A) and 8(B) provides an illustration showing use of the device for determining detection error. For each data point, the device was positioned according to a row in the pre-determined offset table, FIG. 7. The position of the device was then determined by the detection and locating protocol and algorithm of the ETx. FIG. 8(A) shows VERT (vertical) Detection Error versus Known Offset. FIG. 8(B) shows ROLL Detection Error versus Known Offset. Shown are detection errors for 50 Data points in each plot against the known offsets FIG. 9 provides an illustration showing use of the device for determining adjustment error. The device was positioned according to a row in the pre-determined offset table, FIG. 7. The ETx was then operated to adjust the robotic table to correct for the offset position detected. FIG. 9(A) shows VERT (vertical) Offset after Robotic Correction versus Known Offset. FIGS. 9(B) to 9(F) show similar data for LONG (longitude), LAT (latitude), YAW, ROLL, and PITCH. Shown are errors in correction or adjustment in 6D for 50 Data points in each plot against the known offsets. About 95% of the Errors lie within the ±1 mM or ±1° range FIGS. 10(A) and 10(B) provide compilation and analysis of 50. Sets of ETRQA Data for detection error and correction error, respectively. Accuracy is given as Mean±SD for each 6D position. In FIG. 10(A), correlation coefficients were small showing there were no significant relation between the final errors and the initial known offsets. Larger correlation coefficients would indicate a detection bias that should be correctable by adjusting the machine. In FIG. 10(B), there were systematic mismatches between Neutral configuration at the LINAC™ and that measured by CT. The data show that in this example, Robotic Correction is affected by the error at the Neutral configuration detection, due to the CT Neutral configuration setting.

The invention has been described and illustrated in this disclosure with reference to particular embodiments for the benefit and convenience of the reader. Discussion of various aspects of the device in the context of image-guided radiation therapy does not limit its use to that context except where expressly indicated.

The devices and methods of the invention may be substituted and adapted for use in different contexts for different objectives using different materials, elements, and steps without undue experimentation, thus achieving any or all of the benefits of the invention without departing from the scope of what is claimed.

In the United States of America and elsewhere as permitted by law, each publication and patent document cited in this disclosure is incorporated into the disclosure by reference in its entirety for all purposes, to the same extent and effect as if each such publication or document was explicitly and individually indicated to be incorporated by reference.

The invention claimed is:

1. A device for calibrating a robotic couch control system, wherein the system comprises a robotic couch, a detecting apparatus for determining the position of an object on the robotic couch, and a microprocessor programmed to control the robotic couch according to its position as measured by the detecting apparatus,
wherein the device comprises:
a) a body configured for disposing on the robotic couch;
b) a plurality of markers affixed on or within the body, wherein each marker is configured so that its position may be determined by the detecting apparatus when the device is disposed on the robotic couch; and
c) means for adjusting and securing the pitch, roll, and yaw of the body in relation to the robotic couch when the body is disposed on the robotic couch.

2. The device of claim 1, wherein the system is configured for image-guided radiation therapy (IGRT) of a target tissue in a patient secured on the robotic couch.

3. The device of claim 1, wherein the detecting apparatus is a computer guided tomography (CT) imaging apparatus.

4. The device of claim 1, wherein the body of the device is configured for securing to the robotic couch by way of a base plate comprising a plurality of feet.

5. The device of claim 1, wherein the markers comprise a plurality of rods, each configured so that the detecting apparatus may determine the rod's position.

6. The device of claim 1, wherein the markers comprise a plurality of ball bearings, each configured so that the detecting apparatus may determine the bearing's position.

7. The device of claim 1, wherein the markers comprise a plurality of infrared spheres for servo-tracking of adjustments of the robotic couch.

8. The device of claim 1, wherein the body is configured to be suspended above the robotic couch by way of a ball joint.

9. The device of claim 8, wherein the ball joint is mounted on a supporting rod disposed upon a base plate that is configured for placing securely upon the robotic couch.

10. The device of claim 8, wherein the body is configured so that its pitch, roll, and yaw in relation to the robotic couch may all be adjusted by pivoting the body on the ball joint.

11. The device of claim 8, wherein the body is configured so that its pitch, roll, and yaw in relation to the robotic couch may be adjusted and secured by way of a plurality of vertically positioned support screws.

12. The device of claim 11, wherein the support screws pass downwards towards a base plate through a lateral support structure projecting from the body.

13. The device of claim 1, wherein both the pitch and roll of the body in relation to the robotic couch may be adjusted and secured within a range of at least 2 degrees either way from a neutral position.

14. The device of claim 1, further comprising a grid for aligning and adjusting the device horizontally on the robotic couch.

15. A calibration system, comprising the device according to claim 1, and one or more inclinometers for determining the pitch and roll of the body in relation to the robotic couch.

16. A calibration system, comprising the device according to claim 1, and two inclinometers, wherein both of the two inclinometers are separate and apart from the body of the device and secured orthogonally in relation to each other.

17. A calibration system, comprising the device according to claim 1, and a microprocessor programmed to obtain and compile information regarding a change in position of the body of the device upon the robotic couch in relation to a previous position, as measured by the detecting device.

18. The calibration system of claim 17, wherein such information is obtained before the robotic couch control system makes adjustments to the position of the robotic couch to compensate for said change in position.

19. The calibration system of claim 17, wherein such information is obtained after the robotic couch control system makes adjustments to the position of the robotic couch to compensate for said change in position.

20. The calibration system of claim 17, wherein the microprocessor is programmed to compile information from a plurality of at least 20 changes in position of the body of the device in relation to the robotic couch, wherein the plurality comprises at least 5 changes wherein the horizontal position of the device is changed by at least 10 mm in any direction, and both the pitch and the roll are changed by at least 2 degrees from on original position.

21. An image-guided radiation therapy (IGRT) apparatus undergoing calibration, comprising:
    a) an IGRT apparatus comprising a robotic couch; and
    b) a device according to claim 2 positioned on the robotic couch.

22. An image-guided radiation therapy (IGRT) apparatus that comprises a robotic couch, a detecting apparatus for determining the position of an object on the robotic couch, and a microprocessor programmed to control the robotic couch according to its position as measured by the detecting apparatus;
    wherein positioned upon the robotic couch is a device that comprises:
    a) a body configured for disposing on the robotic couch;
    b) a plurality of markers affixed on or within the body, wherein each marker is configured so that its position may be determined by the detecting apparatus when the device is disposed on the robotic couch; and
    c) means for adjusting and securing the pitch, roll, and yaw of the body in relation to the robotic couch when the body is disposed on the robotic couch.

23. A method for calibrating an image-guided radiation therapy (IGRT) apparatus,
    wherein the IGRT apparatus comprises robotic couch, a detecting apparatus for determining the position of an object on the robotic couch, and at least one radiation source,
    where in the method comprises:
    a) securing a device according to claim 1 upon the couch at an original position;
    b) operating the IGRT apparatus so that it determines the position of the device at the original position;
    c) repositioning and securing the device upon the couch at a new position;
    d) operating the IGRT apparatus so that it determines changes in the pitch, roll, yaw, and horizontal position of the device at the new position in relation to the original position;
    e) determining changes in the pitch, roll, yaw, and horizontal position of the device at the new position in relation to the original position, wherein said determining is independent of the IGRT apparatus; and
    f) comparing the changes determined by the IGRT apparatus in step d) with the changes determined independently of the IGRT apparatus in step e).

24. A method for calibrating an image-guided radiation therapy (IGRT) apparatus,
    wherein the IGRT apparatus comprises robotic couch, a detecting apparatus for determining the position of an object on the robotic couch, and at least one radiation source,
    wherein in the method comprises:
    a) securing a device according to claim 1 upon the couch at an original position;
    b) operating the IGRT apparatus so that it determines the position of the device at the original position;
    c) repositioning and securing the device upon the couch at a new position;
    d) operating the IGRT apparatus so that it adjusts the position of the robotic couch to compensate for changes in the pitch, roll, yaw, and horizontal position of the device at the new position in relation to the original position
    e) determining changes in the pitch, roll, yaw, and horizontal position of the device at the new position in relation to the original position, wherein said determining is independent of the IGRT apparatus.

25. The method of claim 24, wherein steps c) to e) are repeated iteratively at least 20 times over a range of at least 10 mm of horizontal variation in both directions and a range of at least 2 degrees of pitch, roll, and yaw in either direction.

* * * * *